United States Patent [19]

Spector

[11] 4,283,011
[45] Aug. 11, 1981

[54] SCENTED STICKER

[76] Inventor: Donald Spector, 380 Mountain Rd., Union City, N.J. 07087

[21] Appl. No.: 70,512

[22] Filed: Aug. 28, 1979

Related U.S. Application Data

[63] Continuation-in-part of Ser. No. 971,380, Dec. 20, 1978.

[51] Int. Cl.³ .............................................. A61L 9/12
[52] U.S. Cl. ...................................... 239/36; 239/56; 239/57
[58] Field of Search ........................ 239/34, 36, 53–57, 239/60; 2/171.2; 63/DIG. 1, DIG. 2

[56] References Cited

U.S. PATENT DOCUMENTS

| 855,984 | 6/1907 | Russell | 239/55 |
|---|---|---|---|
| 1,988,141 | 1/1935 | Schaller | 239/55 |
| 2,256,917 | 9/1941 | Woiwode et al. | 239/53 |
| 2,615,754 | 10/1952 | Lindenberg | 239/36 |
| 2,626,833 | 1/1953 | Valentine | 239/36 |
| 3,575,345 | 4/1971 | Buck, Jr. | 239/34 |
| 3,896,995 | 7/1975 | Lelicoff | 239/36 |
| 4,158,440 | 6/1979 | Sullivan et al. | 239/56 |

Primary Examiner—Robert B. Reeves
Assistant Examiner—Michael J. Forman
Attorney, Agent, or Firm—Michael Ebert

[57] ABSTRACT

A scented sticker attachable to an article of clothing or other surface, the sticker including an appliqué sheet which is profiled to simulate the appearance of an odoriferous object such as a fruit or flower. Secured to the rear of the sheet is a shallow dish containing a pad saturated with a volatile scent whose odor simulates the characteristic natural odor of the object pictured by the sheet, the scent being emitted through perforations in the sheet. The base of the dish has a layer of pressure-sensitive adhesive thereon to facilitate attachment of the sticker.

4 Claims, 5 Drawing Figures

U.S. Patent  Aug. 11, 1981  4,283,011
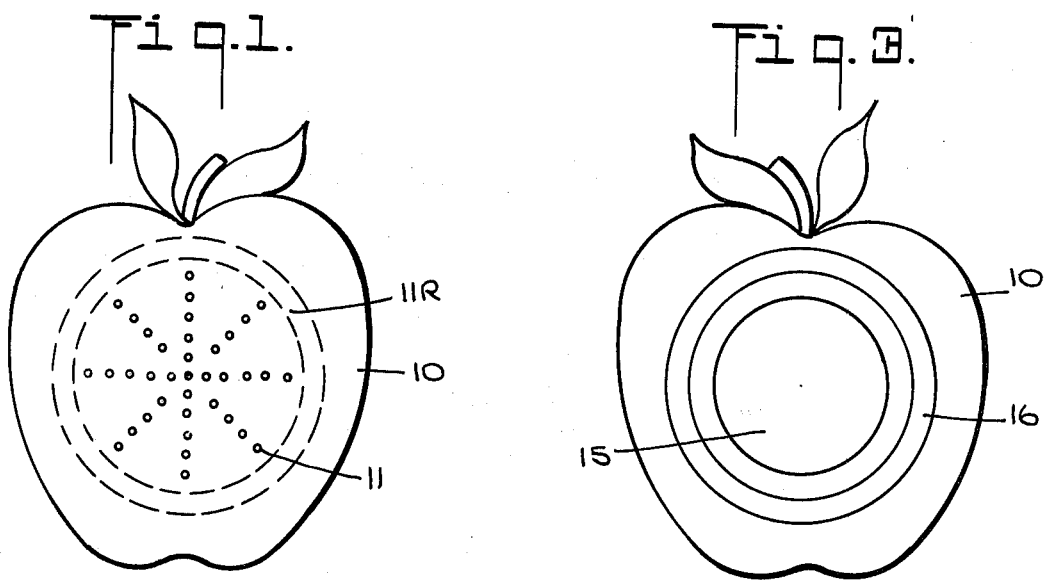
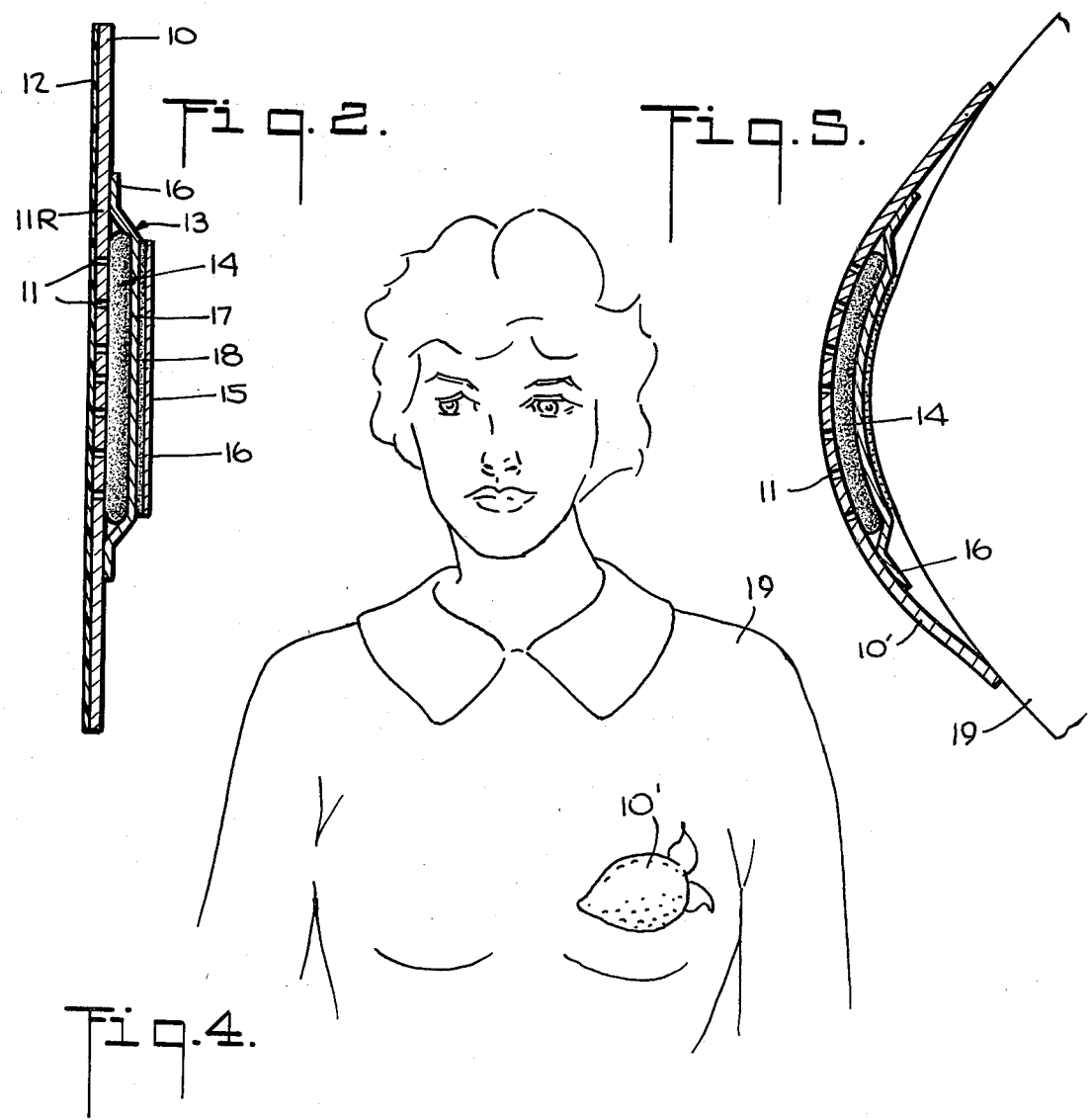

SCENTED STICKER

RELATED APPLICATION

This application is a continuation-in-part of my pending application Ser. No. 971,380, filed Dec. 20, 1978, entitled "Self-Stick Aroma Dispensing Tab."

BACKGROUND OF INVENTION

This invention relates generally to aroma-dispensing stickers that are attachable to an article of clothing or any other surface, and more particularly to a sticker having an appliqué sheet which is contoured and otherwise formed to represent an odoriferous object such as a fruit or flower, the scent dispensed by the sticker simulating the characteristic natural odor of this object.

As used herein, the terms "aroma" and "scent" are not limited to pleasant or savory fragrances but encompass all known odors, whether agreeable or offensive, which are characteristic of odoriferous objects. The term "odoriferous object" includes not only cooked foods and fruits, but animals such as skunks, which exude easily recognized and distinctive odors.

Aroma-producing chemicals are incorporated in numerous products on the market: cosmetics, soaps, scented papers, tobacco and many types of household products. Though most chemical aromas are created with a pleasing effect in mind, other functions are served thereby. Thus it is the common practice to add to an otherwise odorless fuel gas which is toxic, a pungent odor which functions to warn those who sense this odor that a gas line leak exists.

It is now possible to chemically-synthesize aromas to set moods, associations and reactions, in addition to these aromas that are aesthetically pleasing but otherwise without meaning.

Volatile oils and other scent-producing substances used in perfumes were originally derived from natural substances. However, once the chemical composition of any of these substances is identified, the same composition, however complex, can in most cases now be duplicated by organic synthesis. Representative of such duplications are the following familiar scents and their related compounds:

Apple—Geranyl
Lemon—Citral
Pine—Bornyl Isovalerate
Strawberry—Ethylmethylpehnyl glycidate.

Currently, a popular practice is to sew, iron on or otherwise attach to T-shirts and other garments ornamental appliqués which usually take the form of fabrics or sheets cut out in decorative patterns. Such appliqués are permanently attached to the article of clothing and cannot readily be removed should the wearer wish to change or discard the appliqué.

It is also known to adhere scent-producing stick-on tabs to articles of clothing. Thus the Lindenberg U.S. Pat. No. 2,615,754 shows a stick-on sachet for a perfume, the sachet adhering to the surface of the clothing. Lelicoff, in U.S. Pat. No. 3,896,995, discloses a stick-on tab which exudes an insect repellent. But the odors produced by such prior art tabs have to relation at all to the configuration of the tabs.

SUMMARY OF INVENTION

In view of the foregoing, the main object of this invention is to provide a scented sticker which has a configuration related to the aroma exuded thereby so that the viewed sticker is more than a decorative simulation of a known form of odoriferous object, but actually smells like the object and therefore makes both an olfactory and a visual impression on the viewer.

Thus one who attaches on an article of clothing a sticker in accordance with the invention, whose appliqué takes the form, say, of a hot-dog on a roll, will give off an odor that simulates a pungent hot-dog or frankfurter. And one whose stick-on appliqué is in the form of a lemon, exudes the distinct odor of a lemon.

Since there is virtually no limit to the smells that can be synthesized, there is similarly no restriction on the odoriferous objects that can be made the subject matter of appliqués in accordance with the invention; for if the appliqué pictures a rose, it will exude the scent of a flower; but if the appliqué represents a bunch of garlic or an onion, the appropriate scent will be emitted and make a memorable impression on those in the smelling range of the sticker.

Also an object of this invention is to provide a scented sticker which may be mass-produced at low cost, for the sticker, regardless of the type of appliqué, makes use of a dish assembly whose form is standardized and remains the same regardless of the appliqué.

Briefly stated, these objects are attained in a scented sticker which includes an appliqué sheet preferably of foil material which can be conformed to the surface to which the sticker is attached, the appliqué being profiled and otherwise formed to represent a given odoriferous object. The appliqué sheet is perforated in the central zone thereof, and its face is covered by a removable seal.

Associated with the appliqué sheet is a dish assembly constituted by a shallow dish having a circular flange which is secured to the rear of the appliqué sheet at a ring zone surrounding the apertured zone, the dish containing a porous pad saturated with a volatile scent which simulates the odor of the object and is emitted through the apertured zone when the seal is removed. The dish has a flat base coated with a pressure-sensitive adhesive layer covered by a peel-off paper, so that the sticker may be pressed against a surface and adhered thereto, after which the appliqué is conformed to the surface.

OUTLINE OF DRAWINGS

For a better understanding of the invention as well as other objects and further features thereof, reference is made to the following detailed description to be read in conjunction with the accompanying drawings, wherein:

FIG. 1 is a front view of a sticker in accordance with the invention, the appliqué being in the form of an apple;

FIG. 2 is a sectional view of the sticker;

FIG. 3 is a rear view of the sticker;

FIG. 4 shows a lemon-shaped sticker on a T-shirt; and

FIG. 5 is a side view of this sticker on the shirt.

DESCRIPTION OF INVENTION

Referring now to FIGS. 1 to 3, there is shown one embodiment of a scent-producing sticker in accordance with the invention, the sticker including an appliqué sheet 10 which is profiled or die-cut to assume the shape of an apple, the graphics on the front face of this sheet representing a typical red or yellow apple. Sheet 10 is made of metal foil material of high reflectivity so that the apple has a bright, conspicuous appearance. The central zone region of the appliqué sheet is provided with concentric circles of perforations 11.

The face of sheet 11 is covered by a removable seal 12 which may be formed of transparent, flexible acetate film having a pressure-sensitive adhesive coating thereon. Seal 12 serves to close apertures 11 so that no scent is emitted therethrough where the sticker is stored, the seal being removed only when the sticker is put to use.

Associated with the applique is a dish assembly constituted by a dish 13, a pad 14 and a release paper 15. Dish 13, which is of shallow construction, is provided with a circular flange 16. This flange is bonded to the rear surface of appliqué sheet 10 at a ring zone 11R which surrounds the central apertured zone 11, to define chamber 17 which is vented through the perforations.

Disposed within chamber 17 is a disc-shaped wafer or pad 14 of absorbent material. This may be a cellulose blotter, a flexible foam plastic or other sponge-like non-reactive substance capable of absorbing a liquid scent. Pad 14 is saturated with a concentrated liquid scent of the desired character, so that a small supply of the liquid is capable of giving off a scent for a prolonged period. Since the appliqué represents an apple in the embodiment illustrated, the scent in this instance simulates the odor of an apple.

The flat base of dish 13 is coated with a layer 18 of pressure-sensitive adhesive which is covered by release paper 15. Thus to attach the sticker to a surface, one has first to peel off the release paper to expose the adhesive.

As shown in FIG. 4, the sticker may be attached to a close-fitting T-shirt 10; in which event, as shown in FIG. 5, the appliqué foil sheet 10, which in this instance has a lemon form, is pressed against the contoured shirt surface and caused to conform thereto. Hence even though the appliqué sheet is held to the shirt by the adhesive layer behind the dish, the sheet is not separated from the shirt but lies thereagainst, except for the bulge in the region of the dish assembly. In this instance, the wearer of the shirt carries a lemon appliqué which smells like a lemon.

In practice, the appliqué sheet of the sticker may represent any odoriferous object and is therefore appropriately profiled and dimensioned. Thus an appliqué realistically representing a cooked hamburger on a roll will be larger than an appliqué showing a full size peach. However, the dish assemblies designed for all appliqués, regardless of their form, are of identical construction, save for the liquid scent saturating the pad which is chosen to simulate the appliqué object for which it is intended. Hence the dish assembly may be mass-produced and inventoried for use in conjunction with appliqués which may be made on a smaller scale in a large range of different object configurations.

While there has been shown and described a preferred embodiment of a scented sticker in accordance with the invention, it will be appreciated that many changes and modifications may be made therein without, however, departing from the essential spirit thereof.

For example, instead of a profiled appliqué sheet covering the dish and attached to the flange thereof, the cover sheet for this purpose can be a simple disc of foil or laminated foil material having the same diameter as the flange and attached thereto. In this alternative embodiment, an odoriferous object such as an apple is graphically printed on the foil or on the face of a paper disc superposed on the foil disc and adhered thereto. And instead of having the cover sheet pre-perforated as in the embodiment illustrated in FIG. 1, in which event the perforations must be sealed, one can by means of a ball point pen or other pointed device, punch holes in the foil disc when the scented sticker is put to use, so that emitted from the chamber pad, which is trapped in the dish, is a scent which simulates the characteristic odor of the object pictured on the disc.

I claim:
1. A scented sticker attachable to an article of clothing or other surface, each sticker comprising:
A an appliqué sheet profiled to simulate an odoriferous object and formed of metal foil conformable to said surface, said sheet having a perforated zone thereon;
B a dish assembly constituted by a shallow dish having a flat base and a flange, said flange being bonded to a ring zone on the rear face of the appliqué sheet which surrounds the perforated zone to define a chamber which is vented through said perforated zone, an absorbent pad disposed in said chamber saturated with a volatile scent whose odor simulates the characteristic odor of said object, said dish assembly and said appliqué sheet being impervious to said volatile scent, and a layer of pressure-sensitive adhesive on said base to attach the base of said dish to said surface, said layer being covered by a removable release paper; and
C a removable seal formed of transparent film material impervious to said volatile scent having a pressure-sensitive adhesive coating thereon secured to said appliqué sheet to cover said apertured zone to prevent emission of said scent until the seal is removed.

2. A sticker as set forth in claim 1, wherein said object is an apple and said scent is that of an apple.

3. A sticker as set forth in claim 1, wherein said object is a lemon and said scent is that of a lemon.

4. A sticker as set forth in claim 1, wherein said pad is a disc-shaped sponge.

* * * * *